(12) United States Patent
Schaffer

(10) Patent No.: US 9,561,308 B2
(45) Date of Patent: Feb. 7, 2017

(54) BIODEGRADABLE COMPOSITE WIRE FOR MEDICAL DEVICES

(75) Inventor: Jeremy E. Schaffer, Leo, IN (US)

(73) Assignee: Fort Wayne Metal Research Products Corporation, Fort Wayne, IN (US)

( * ) Notice: Subject to any disclaimer, the term of this patent is extended or adjusted under 35 U.S.C. 154(b) by 751 days.

(21) Appl. No.: 13/168,579

(22) Filed: Jun. 24, 2011

(65) Prior Publication Data

US 2011/0319978 A1  Dec. 29, 2011

Related U.S. Application Data

(60) Provisional application No. 61/358,674, filed on Jun. 25, 2010, provisional application No. 61/466,627, filed on Mar. 23, 2011.

(51) Int. Cl.
*A61F 2/82*  (2013.01)
*A61L 31/02*  (2006.01)
(Continued)

(52) U.S. Cl.
CPC ............ *A61L 31/022* (2013.01); *A61L 31/088* (2013.01); *A61L 31/148* (2013.01); *Y10T 29/49826* (2015.01)

(58) Field of Classification Search
CPC ....................................................... A61F 2/82
(Continued)

(56) References Cited

U.S. PATENT DOCUMENTS 5,607,442 A  3/1997  Fischell et al.
5,628,787 A  5/1997  Mayer
(Continued)

FOREIGN PATENT DOCUMENTS

EP  1334701 A2  8/2003
EP  2186492 A1  5/2010
(Continued)

OTHER PUBLICATIONS

"Structure-Property Relationship in Conventional and Nanocrystalline NiTi Intermetallic Alloy Wire", Schaffer, Journal of Materials Engineering and Performance, vol. 18 (5-6) Aug. 2009, pp. 582-587 (Schaffer 4).
(Continued)

*Primary Examiner* — Matthew Schall
(74) *Attorney, Agent, or Firm* — Faegre Baker Daniels LLP

(57) ABSTRACT

A bimetal composite wire including, in cross-section, an outer shell or tube formed of a first biodegradable material and an inner core formed of a second biodegradable material. When formed into a stent, for example, the first and second biodegradable materials may be different, and may have differing biodegradation rates. In a first embodiment, the first biodegradable material of the shell may degrade relatively slowly for retention of the mechanical integrity of a stent during vessel remodeling, and the second biodegradable material of the core may degrade relatively quickly. In a second embodiment, the first biodegradable material of the shell may degrade relatively quickly, leaving a thinner structure of a second biodegradable material of the core that may degrade relatively slowly. The biodegradation rates may be inherently controlled, such as by selection of materials, and also may be mechanically controlled, such as by material thicknesses and the geometric configuration of the shell, core, or overall device. In any embodiment, the metallic scaffold may also be coated with a drug-eluting, biodegradable polymer, to further inhibit neointimal proliferation and/or restenosis.

20 Claims, 11 Drawing Sheets

(51) Int. Cl.
*A61L 31/08* (2006.01)
*A61L 31/14* (2006.01)

(58) Field of Classification Search
USPC ........................................................ 623/1.38
See application file for complete search history.

(56) References Cited

U.S. PATENT DOCUMENTS

| | | |
|---|---|---|
| 6,287,332 B1 | 9/2001 | Bolz et al. |
| 6,364,902 B1 | 4/2002 | Dickenson et al. |
| 6,799,357 B2 | 10/2004 | Webb et al. |
| 6,854,172 B2 | 2/2005 | Kaese et al. |
| 7,020,947 B2 | 4/2006 | Bradley |
| 7,294,214 B2 | 11/2007 | Craig |
| 7,420,124 B2 | 9/2008 | Michael et al. |
| 7,452,501 B2 | 11/2008 | Furst et al. |
| 7,452,502 B2 | 11/2008 | Furst et al. |
| 7,501,579 B2 | 3/2009 | Michael et al. |
| 7,641,983 B2 | 1/2010 | Stinson |
| 7,651,527 B2 | 1/2010 | Krivoruchko et al. |
| 7,745,732 B2 | 6/2010 | Michael et al. |
| 7,780,798 B2 | 8/2010 | Stinson et al. |
| 2002/0004060 A1 | 1/2002 | Heublein et al. |
| 2004/0098108 A1 | 5/2004 | Harder et al. |
| 2006/0052863 A1 | 3/2006 | Harder et al. |
| 2006/0276875 A1 | 12/2006 | Stinson et al. |
| 2007/0156231 A1 | 7/2007 | Weber |
| 2007/0282432 A1 | 12/2007 | Stinson et al. |
| 2008/0015578 A1 | 1/2008 | Erickson et al. |
| 2008/0082162 A1 | 4/2008 | Boismier et al. |
| 2008/0086199 A1 | 4/2008 | Dave et al. |
| 2008/0312736 A1 | 12/2008 | Mueller et al. |
| 2009/0024211 A1 | 1/2009 | Wittchow |
| 2009/0030500 A1 | 1/2009 | Weber et al. |
| 2009/0069884 A1 | 3/2009 | Mueller |
| 2009/0081313 A1 | 3/2009 | Aghion et al. |
| 2009/0164002 A1 | 6/2009 | Becher et al. |
| 2009/0171452 A1 | 7/2009 | Yamamoto et al. |
| 2009/0192596 A1 | 7/2009 | Adden |
| 2009/0198320 A1 | 8/2009 | Mueller et al. |
| 2009/0204203 A1 | 8/2009 | Allen et al. |
| 2009/0240323 A1 | 9/2009 | Wilcox |
| 2009/0260852 A1 | 10/2009 | Schaffer |
| 2009/0297883 A1 | 12/2009 | Koppensteiner et al. |
| 2010/0004733 A1 | 1/2010 | Atanasoska et al. |
| 2010/0075162 A1 | 3/2010 | Yang et al. |
| 2010/0082092 A1 | 4/2010 | Gerold |
| 2010/0087911 A1 | 4/2010 | Mueller |
| 2010/0087914 A1 | 4/2010 | Bayer et al. |
| 2010/0087916 A1 | 4/2010 | Bayer et al. |
| 2010/0106243 A1 | 4/2010 | Wittchow |
| 2010/0161031 A1 | 6/2010 | Papirov et al. |
| 2010/0161053 A1 | 6/2010 | Bayer |
| 2010/0198332 A1 | 8/2010 | Gerold |
| 2010/0292776 A1 | 11/2010 | Weber et al. |
| 2011/0319977 A1 | 12/2011 | Pandelidis et al. |
| 2012/0143227 A1 | 6/2012 | Steckel et al. |

FOREIGN PATENT DOCUMENTS

| | | |
|---|---|---|
| EP | 1492580 B1 | 6/2012 |
| WO | WO2010096516 A2 | 8/2010 |
| WO | WO2010/132244 A2 | 11/2010 |

OTHER PUBLICATIONS

International Search Report and Written Opinion mailed Aug. 19, 2011 in International Application No. PCT/US2011/041835.
D'Souza et al. "Biodegradable Stents—A New Era?" European Cardiology [Online] 2008, 4, pp. 82-84.
Fischer et al. "Metallic Biomaterials for Coronary Stents" Zeitschrift für Kardiologie [Online] 2001, 90, pp. 251-262.
Hermawan et al. "Degradable Metallic Biomaterials: Design and Development of Fe—Mn Alloys for Stents" Journal of Biomedical Materials Research Part A [Online] 2010, 39A, pp. 1-11.
Hermawan et al. "Developments in Metallic Biodegradable Stents" Acta Biomaterialia [Online] 2010, 6, pp. 1693-1697.
Hermawan et al. "Fe—Mn Alloys for Metallic Biodegradable Stents: Degradation and Cell Viability Studies" Acta Biomaterialia [Online] 2010, 6, pp. 1852-1860.
Moravej et al. "Electroformed Iron as New Biomaterial for Degradable Stents: Development Process and Structure-Properties Relationship" Acta Biomaterialia [Online] 2010, 6, pp. 1726-1735.
Waksman et al. "Safety and Efficacy of Bioabsorbable Magnesium Alloy Stents in Porcine Coronary Arteries" Catheterization and Cardiovascular Interventions [Online] 2006, 68, pp. 607-619—Abstract only.
Wang et al. "Mechanical Analysis on a New Type of Biodegradable Magnesium-Alloy Stent" Sheng Wu Yi Xue Gong Cheng Xue Za Zhi / Journal of Biomedical Engineering [Online] 2009, 26, pp. 338-341—Abstract only.
Wu et al. "Finite Element Shape Optimization for Biodegradable Magnesium Alloy Stents" Annals of Biomedical Engineering [Online] 2010, 38, pp. 2829-2840.
Zhu et al. "Development of Biodegradable Magnesium-Based Biomaterials" Sheng Wu Yi Xue Gong Cheng Xue Za Zhi / Journal of Biomedical Engineering [Online] 2009, 26, pp. 437-439—Abstract only.
DiMario et al. "Drug-Eluting Bioabsorbable Magnesium Stent" Jounral of Interventional Cardiology, vol. 17, No. 6, 2004, pp. 391-395.

BIODEGRADABLE COMPOSITE WIRE FOR MEDICAL DEVICES

CROSS-REFERENCE TO RELATED APPLICATIONS

This application claims the benefit under Title 35, U.S.C. §119(e) of U.S. Provisional Patent Application Ser. No. 61/358,674, filed on Jun. 25, 2010, entitled BIODEGRADABLE COMPOSITE WIRE FOR MEDICAL DEVICES, and U.S. Provisional Patent Application Ser. No. 61/466,627, filed on Mar. 23, 2011, entitled BIODEGRADABLE COMPOSITE WIRE FOR MEDICAL DEVICES, the disclosures of each are expressly incorporated herein in their entireties.

BACKGROUND

1. Technical Field

The present invention relates to wire used in biomedical applications and, in particular, relates to a biodegradable composite wire for use in medical devices such as stents.

2. Description of the Related Art

Stents are artificial tube-like structures that are deployed within a conduit or passage in the body to alleviate a flow restriction or constriction. Stents are commonly used in coronary arteries to alleviate blood flow restrictions resulting, e.g., from cardiovascular disease. However, stents may also be used in non-coronary vessels, the urinary tract and other areas of the body. Non-coronary applications range broadly from compliant pulmonary vessels of children with congenital heart disease (CHD), to atherosclerotic popliteal arteries of older patients with critical limb ischemia (CLI). Stented lesions may be long and tortuous as in the case of severe infrainguinal lesions, or short and relatively uniform as in mild pulmonary artery stenoses.

Examples of non-coronary stent applications include arteriovenous fistulas (AVFs) or false aneurysms, which may occur as a result of trauma due to gunshot wounds, falling accidents, or other blunt force incident. Such phenomena often occur in the upper limbs of the body where lack of perfusion can manifest as gangrene, severe pain, or local cyanosis. Critical limb ischemia associated with atherosclerosis can also result in the need for radial or axillary artery stenting, for example, to avoid amputation or other more serious morbidities. In contrast to most thoracoabdominal implantation sites (such as in coronary arteries), upper and lower limb anatomy is typically subjected to greater range of motion, thereby potentially increasing mechanical fatigue.

Typically, stents are made of either biocompatible metal wire(s) or polymeric fiber(s) which are formed into a generally cylindrical, woven or braided structure of the type shown in FIGS. 1A and 1B. These types of stents are typically designed to be either "self-expanding", in which the stent may be made of a shape memory material, for example, and deploys automatically by expanding upon removal of a constricting force when released from a containment device, or "balloon-expanding", in which the stent is forcibly expanded from within by an inflatable balloon.

When a stent is implanted, it applies a radial force against the wall of the vessel in which it is implanted, which improves vessel patency and reduces acute closure or increases vessel diameter. In either case, the vessel usually achieves a new equilibrium by biological remodeling of the vessel wall over a period of weeks or months. After such remodeling is complete, the stent may no longer be needed for mechanical support and could potentially inhibit further natural positive remodeling of the vessel or limit re-intervention, for example. However, removal of the stent may be difficult.

Many known stents are formed of corrosion-resistant and substantially non-biodegradable or non-bioresorbable metal materials which maintain their integrity in the body for many years after implantation. Design efforts for creating bioabsorbable stents have focused primarily on balloon-expandable technology for coronary pathologies, and may include polymer biodegradable stents using poly-L lactic acid (PLLA) and poly-L glycolic acid (PLGA), nutrient metals of magnesium (Mg), including alloys or powder metallurgy forms of magnesium, and iron (Fe), and iron-manganese alloys. Some research methods have also focused on hybrids including layered biodegradable polymers and bioabsorbable polymer coated nutrient metals. While such materials are resorbable, they may have low mechanical strength and resilience, and/or may confer inadequate control over the rate of bioabsorption (i.e., by biodegrading too slowly or quickly in vivo).

What is needed is a biodegradable metallic wire with sufficient mechanical properties and appropriate degradation rates for use in biomedical applications, which represents an improvement over the foregoing.

SUMMARY

The present invention provides a composite wire including, in cross-section, an outer shell or tube formed of a first biodegradable material and an inner core formed of a second biodegradable material, both of which are adapted to resorb or disappear after post-operative vessel healing has occurred and vessel patency has been restored. When formed into a stent, for example, the first and second biodegradable materials may be different, and may have differing biodegradation rates. The first biodegradable material may degrade relatively slowly for retention of the mechanical integrity of the stent during vessel remodeling, and the second biodegradable material may degrade relatively quickly. The biodegradation rates may be inherently controlled, such as by selection of materials, and also may be mechanically controlled, such as by material thicknesses and the geometric configuration of the shell, core, or overall device.

Materials suitable for use in the composite wire include nutrient-metal-composites and alloys of pure iron, manganese, magnesium, and zinc. Particular metals or metal alloys may be selected to provide a desired biodegradation rate and mechanical properties. In one embodiment, the first material may be pure Fe, an Fe—Mn alloy, or another Fe-based alloy which degrades relatively slowly upon exposure to biological media, and the second material may be pure Mg or an Mg-based alloy which, once exposed by biodegradation of the first material, degrades relatively quickly. The total rate of biodegradation of the wire, and therefore the duration of the overall mechanical integrity of the wire, is controlled by the relative thicknesses of the first and second materials or, alternatively stated, by the relative cross-sectional areas of the outer sheath and core material relative to the overall cross-sectional area of the wire.

The rate of proliferation of smooth muscle cells (SMC) may be influenced by the presence of matter which changes the local environment surrounding the cell. The implantation of pure iron stents in porcine arteries has been shown to reduce SMC proliferation, without negative consequence, and may provide a reduction in late negative remodeling or restenosis. A smooth muscle cell proliferation-inhibiting ferrous outer shell disposed over a relatively quickly biodegrading Mg or Mg-alloy core may provide the same SMC proliferation-inhibition, thereby mitigating late closure.

The mechanical strength of the wire may be controlled to impart either a self-expanding character to a braided or knit stent device made from the wire, or may be controlled to provide a high strength wire for use in balloon-expandable wire-based stents. The mechanical strength and elastic resilience of the wire can be significantly impacted through thermomechanical processing.

The present composite wire provides a novel mode of biodegradation rate control, as well as high strength properties suitable for use in applications such as intravascular stents, particularly stents used in non-coronary vasculature, as well as other applications such as emboli-collecting devices and emboli-diverting blood filters of the type used, for example, to prevent ischemic stroke within the brain during high risk vascular surgical procedures.

In one form thereof, the present invention provides a bimetal composite wire including an outer shell formed of a first biodegradable metallic material; and an inner core formed of a second biodegradable metallic material, the first and second biodegradable metallic materials being different from one another whereby the first and second biodegradable metallic materials have differing biodegradation rates.

In the bimetal composite wire, the first biodegradable material may be selected from the group consisting of pure metallic iron (Fe) and an iron-based alloy (Fe alloy), and the second biodegradable material may be selected from the group consisting of pure magnesium (Mg) and a magnesium-based alloy (Mg alloy), or the first biodegradable material may be selected from the group consisting of pure magnesium (Mg) and a magnesium-based alloy (Mg alloy), and the second biodegradable material may be selected from the group consisting of pure metallic iron (Fe) and an iron-based alloy (Fe alloy).

The bimetal composite wire may have one or more of: a ratio of yield strength to elastic modulus of at least 0.5%, a fatigue strength of $10^7$ cycles at an alternating strain level of 0.2, and a ductility characterized by the ability to form the wire over a mandrel diameter equal to or less than 20 times the outside diameter of the bimetal composite wire.

A stent may be formed of the bimetal composite wire.

In another form thereof, the present invention provides a method of manufacturing a wire, including the steps of providing an outer shell made of a first biodegradable material; inserting a core into the outer shell to form a wire construct, the core formed of a second biodegradable material, the first and second biodegradable materials being different from one another; and imparting cold work at room temperature to the wire construct by drawing the wire construct from a first outer diameter to a second outer diameter less than the first outer diameter.

After the imparting step, the method may include the additional step of annealing the wire construct by heat treatment. With one of the first and second biodegradable materials having a melt temperature higher than the other of the first and second biodegradable materials, the annealing step may be conducted at a temperature not exceeding 50% of the higher melt temperature.

The method may further include the additional step of forming the wire into a stent.

The first biodegradable material may be selected from the group consisting of pure metallic iron (Fe) and an iron-based alloy (Fe alloy), and the second biodegradable material may be selected from the group consisting of pure magnesium (Mg) and a magnesium-based alloy (Mg alloy), or the first biodegradable material may be selected from the group consisting of pure magnesium (Mg) and a magnesium-based alloy (Mg alloy), and the second biodegradable material may be selected from the group consisting of pure metallic iron (Fe) and an iron-based alloy (Fe alloy).

In a further form thereof, the present invention provides a stent formed of a wire selected from the group consisting of iron and iron alloy, the wire having a yield strength of at least 1375 MPa. The wire may be formed of an iron-manganese alloy.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1A:
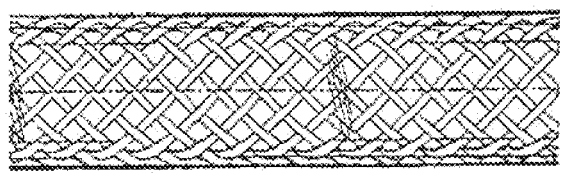
FIGS. 1A and 1B are perspective views of known stents.

Corresponding reference characters indicate corresponding parts throughout the several views. Although the exemplifications set out herein illustrate embodiments of the invention, the embodiments disclosed below are not intended to be exhaustive or to be construed as limiting the scope of the invention to the precise form disclosed.

DETAILED DESCRIPTION

The present disclosure provides bioabsorbable wires which produce dilatational force sufficient to promote arterial remodeling and patency, while also being capable of fully biodegrading over a specified period of time. This controlled biodegradation promotes endothelial vasoreactivity, improved long term hemodynamics and wall shear stress conditions, enablement of reintervention and accommodation of somatic growth, and mitigates fracture risk over the long term.

As used herein, "biodegradable" refers to a material that is able to be chemically broken down in a physiological environment, i.e., within the body or inside body tissue, by processes such as resorbtion or absorption, which will generally result in the complete degradation of the appliance within a period of weeks to months, such as 18 months or less, 24 months or less, or 36 months or less, for example. This rate stands in contrast to more "degradation-resistant" or permanent appliances, such as those constructed from Ni—Ti or stainless steel, which remain in the body, structurally intact, for a period exceeding at least 36 months and potentially throughout the lifespan of the recipient. Biodegradable metals used herein include nutrient metals, i.e., metals such as iron, magnesium, and manganese, that have biological utility and are used by, or taken up in, biological pathways.

As used herein, "fatigue strength" refers to the load level at which the material meets or exceeds a given number of load cycles to failure. Herein, the load level is given as alternating strain, as is standard for displacement or strain-controlled fatigue testing, whereby terms are in agreement with those given in ASTM E606.

As used herein, a "load cycle" is one complete cycle wherein the unloaded (neutral) material is loaded in tension to a given alternating stress or strain level, unloaded, loaded again in compression to the same alternating stress or strain level, and returned to the neutral, externally unloaded position.

As used herein, "alternating strain" refers to the difference between the mean strain and the minimum strain level or the difference between the maximum strain and the mean strain in a strain-controlled fatigue cycle, where units are non-dimensional and given as percent engineering strain.

As used herein, "engineering strain" is given non-dimensionally as the quotient where the differential length associated with the load is the dividend and original length the divisor.

As used herein, "resilience" refers to an approximate quantification of the uniaxial elastic strain capability of a given wire test sample, and is calculated as the quotient of yield strength and modulus of elasticity, wherein yield strength is the dividend and modulus the divisor. Units: non-dimensional.

As used herein, "elastic modulus" is defined as Young's modulus of elasticity and is calculated from the linear portion of the tensile, monotonic, stress-strain load curve using linear extrapolation via least squares regression, in accordance with ASTM E111. Units are stress, in gigapascals (GPa).

As used herein, "yield strength", in accordance with ASTM E8, refers to the 0.2% offset yield strength calculated from the stress-strain curve and gives quantitative indication of the point at which the material begins to plastically deform. Units are stress, in megapascals (MPa).

As used herein, "ultimate strength", in accordance with ASTM E8, refers to the maximum engineering stress required to overcome in order to rupture the material during uniaxial, monotonic load application. Units are stress, in megapascals (MPa).

As used herein, "elongation" is the total amount of strain imparted to a wire during a uniaxial, monotonic tensile test, en route to specimen rupture, and is defined herein in accordance with ASTM E8. Units are non-dimensional, and are given as a percentage strain relative to the original specimen length.

As used herein, "energy to rupture" or "modulus of toughness" is defined herein as the amount of energy required to rupture a wire in a uniaxial tensile test. In a graphical stress-strain representation, the energy to rupture, as quantified herein, is the area under the curve for a given material. Units: millijoules per cubic millimeter (mJ/mm$^3$).

As used herein, "magnesium ZM21" refers to magnesium ZM21 alloy, otherwise known as ZM-21 or simply ZM21 alloy, which is a medium-strength forged Magnesium alloy comprising 2 wt % Zn, 1 wt % Mn and a balance of Mg.

"Fe(II)" refers to iron ions of charge 2+ that may be associated with degradation products in a saline or bodily environment of iron or iron based alloys.

"Fe(III)" refers to iron ions of charge 3+ that may be associated with degradation products in a saline or bodily environment of Fe or Fe-based alloys.

"Mg(II)" refers to magnesium ions of charge 2+ that may be associated with degradation products in a saline or bodily environment of Mg or Mg-based alloys.

"RE" is used here to signify the rare earth elements given in the periodic table of elements and including elements such as Scandium, Yttrium, and the fifteen lanthanides, i.e. La, Ce, Pr, Nd, Pm, Sm, Eu, Gd, Tb, Dy, . . . , to Lu.

"Nitinol" is a trade name for a shape memory alloy comprising approximately 50 atomic % Nickel and balance Titanium, also known as NiTi, commonly used in the medical device industry for highly elastic implants.

"DFT®" is a registered trademark of Fort Wayne Metals Research Products Corp. of Fort Wayne, Ind., and refers to a bimetal or poly-metal composite wire product including two or more concentric layers of metals or alloys, typically at least one outer layer disposed over a core filament formed by drawing a tube or multiple tube layers over a solid metallic wire core element.

"Smooth muscle cells" (SMC) refer to mammalian cells of the smooth muscle that constitutes the vasotone-controlling muscle layer in, e.g., murine, porcine, human blood vasculature.

"OD" refers to the outside diameter of a metallic wire or outer shell.

"ID" refers to the inside diameter of a metallic outer shell.

Wire Construction

Figure 2:
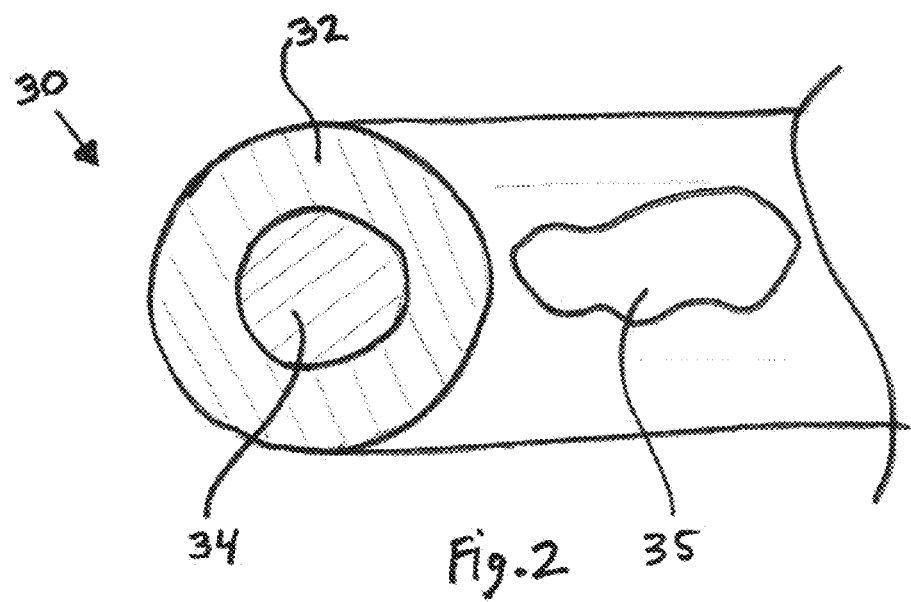
FIG. 2 is a partial cross-sectional view of a composite wire made in accordance with the present invention.

Referring to FIG. 2, a bimetallic composite wire 30 is shown in accordance with the present invention, which has a circular cross section and extends along a longitudinal axis and includes outer shell, sheath, or tube 32 made of a first biodegradable material and a core 34 made of a second biodegradable material. Outer shell 32 may be formed as a uniform and continuous surface or jacket, such that wire 30 may be coiled, braided, or stranded as desired.

The first biodegradable material of outer shell 32 may be pure metallic iron (Fe), an anti-ferromagnetic iron-manganese alloy (Fe—Mn) such as Fe-30Mn or Fe-35Mn, or another iron-based alloy (Fe alloy), and the second biodegradable material or core 34 may be pure magnesium (Mg) or a magnesium-based alloy (Mg alloy) such as ZM21 (Mg-2Zn-1Mn), AE21 (Mg-2Al-1RE, where RE is any of the Rare Earth metals such as Sc, Y, and the fifteen lanthanides, i.e., La, Ce, Pr, Nd, Pm, Sm, Eu, Gd, Tb, Dy . . . to Lu), AE42 (Mg-4Al-2RE), WE43 (Mg-4Y-0.6Zr-3.4RE, as in Yttrium, Zirconium, RE). Generally, for equal amounts of the first and second biodegradable materials, the first biodegradable material will degrade in vivo at a slower rate than the second biodegradable material though, as discussed below, the relative degradation rates may be varied by providing wire constructs having varying amounts of the first and second biodegradable materials.

Exemplary bimetal composite wires, discussed in detail in the Examples section below, are expressed as a first material and a second material comprising a specified balance percentage of the total wire cross-sectional area. For example, exemplary wires may include the following material compositions: Fe-DFT-25% Mg (75% iron and 25% magnesium, which may also be referred to in the present disclosure as Fe-DFT-25Mg, Fe-25% Mg, or Fe-25Mg); Fe-DFT-57% Mg (43% iron and 57% magnesium, which may also be referred to in the present disclosure as Fe-DFT-57Mg, Fe-57% Mg, or Fe-57Mg); and Fe35Mn-DFT-25% MgZM21 (75% iron manganese and 25% magnesium ZM21, which may also be referred to in the present disclosure as Fe35Mn-DFT-25Mg, Fe35Mn-25MgZM21, or Fe35Mn-25Mg).

It is contemplated that outer shell 32 and core 34 may be formed from the same material or different materials, and that either shell 32 or core 34 may be formed from any of the above-mentioned materials as required or desired for a particular application. For example, shell 32 may be formed of the first biodegradable material with core 34 formed of the second biodegradable material. In these embodiments, the material of shell 32 will biodegrade at a slower rate than the material of core 34. In other embodiments, this arrangement may be reversed, wherein shell 32 may be formed of the second biodegradable material and core 34 may be formed of the first biodegradable material and wherein, in these embodiments, the material of shell 32 will biodegrade at a faster rate than the material of core 34.

Control over the rate of biodegradation confers substantial advantages in the design of bioabsorbable stents. For example, a known, controllable wire degradation rate helps avoid downstream embolization by debris, and facilitates optimal control over post-procedural recoil. The in vivo degradation rate governs the time course over which natural vessel-wall loads are transferred from the stent to the vessel, and control over such rate allows stent degradation to be complimentary to the healing process. The lesion healing rate is known to depend upon, among other factors, the age of the patient, disease state, and anatomical location for therapy. Stents made from wire produced in accordance with the present disclosure provide well-designed control over the degradation rate, thereby facilitating therapeutic optimization.

To form wire 30, core 34 is inserted within shell 32 to form a wire construct, and an end of the wire construct is then tapered to facilitate placement of the end into a drawing die. The end protruding through the drawing die is then gripped and pulled through the die to reduce the diameter of the construct and bring the materials into physical contact. After drawing, the inner diameter of the shell will close on the outer diameter of the core such that the inner diameter of the shell will equal the outer diameter of the core whereby, when viewed in section, the inner core will completely fill the outer shell.

The step of drawing subjects wire 30 to cold work. More particularly, drawing imparts cold work to the material of both shell 32 and core 34, with concomitant reduction in the cross-sectional area of both materials. The total cold work imparted to the material during the drawing step can be characterized by the following formula (I):

$$cw = 1 - \left(\frac{D_2}{D_1}\right)^2 \quad (I)$$

wherein "cw" is cold work defined by reduction of the original material area, "$D_2$" is the diameter of the wire after the draw or draws, and "$D_1$" is the diameter of the wire prior to the same draw or draws.

Figure 3:
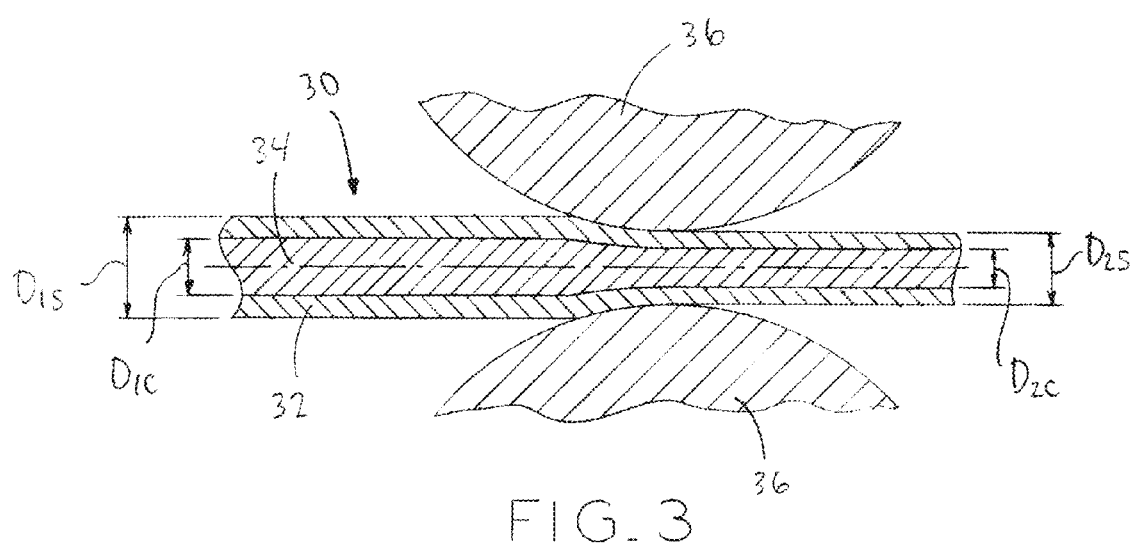
FIG. 3 is a schematic view illustrating an exemplary forming process of composite wire using a lubricated drawing die.

Referring to FIG. 3 the cold work step is performed by drawing wire 30 through a lubricated die 36 (FIG. 5) having a an output diameter $D_2$, which is less than diameter $D_1$ of the undrawn wire 30. Alternatively, wire 30 may be cold-swaged, rolled flat or into other shapes which result in the net accumulation of cold work. Cold work may also be imparted by any combination of techniques including the techniques described here, for example, cold-swaging followed by drawing through a lubricated die finished by cold rolling into a ribbon or sheet form or other shaped wire forms. In one exemplary embodiment, the cold work step by which the diameter of wire 30 is reduced from $D_1$ to $D_2$ is performed in a single draw and, in another embodiment, the cold work step by which the diameter of wire 30 is reduced from $D_1$ to $D_2$ is performed in multiple draws which are performed sequentially without any annealing step therebetween.

The drawing process is repeated, with each subsequent drawing step further reducing the cross section of wire 30 proportionately, such that the ratio of the sectional area of core 34 to the overall sectional area of wire 30 is nominally preserved as the overall sectional area of wire 30 is reduced. Referring to FIG. 3, the ratio of pre-drawing core outer diameter $D_{1C}$ to pre-drawings shell outer diameter $D_{1S}$ is the same as the corresponding ratio post-drawing. Stated another way, $D_{1C}/D_{1S}=D_{2C}/D_{2S}$.

Thermal stress relieving, otherwise known in the art as annealing, at a nominal temperature not exceeding the melting point of either the first or second materials, is used to improve the ductility of the fully dense composite between drawing steps, thereby allowing further plastic deformation by subsequent drawing steps. Further details regarding wire drawing are discussed in U.S. patent application Ser. No. 12/395,090, filed Feb. 27, 2009, entitled "Alternating Core Composite Wire", assigned to the assignee of the present invention, the entire disclosure of which is incorporated by reference herein.

The softening point of the present materials is controlled by introducing cold work into the composite structure after joining the metals. Deformation energy is stored in the structure which serves to reduce the amount of thermal energy required for stress relief, in the present exemplary embodiment, of the iron or iron alloy component. This processing facilitates annealing of the composite structure at temperatures in the range of 40 to 50% of the melting point of the iron or iron alloy component in a manner sufficient to provide ductility to both metal species and successful fine wire production. Such ductility facilitates spooling of the wire, as discussed below, and renders the wire suitable for in vivo uses where low ductility would be undesirable.

Magnesium and its alloys generally comprise a hexagonal-close-packed (hcp) crystal structure which possesses low ductility at room temperature due to intrinsically limited slip systems, primarily confined to the basal plane. For this reason, elevated temperatures are generally used to forge and/or otherwise shape these materials. Such warm-working temperatures generally exceed about 400K. In order to maximize the mechanical properties of the iron or iron-alloy, it is desirable to process these bi-metal composites by cold-working methods, that is, by effecting wire drawing reduction at near room temperature, e.g. 20-30° C. In the present exemplary embodiments, the iron or iron-alloy sheath serves to confine the Mg or Mg-alloy core during wire-drawing, inducing a compressive stress during deformation and confining the material after it exits the drawing die. This processing technique enables cold-drawing of these materials and therefore promotes maximization of mechanical properties by eliminating stress-relief that could otherwise occur during higher temperature processing.

Figure 1B:
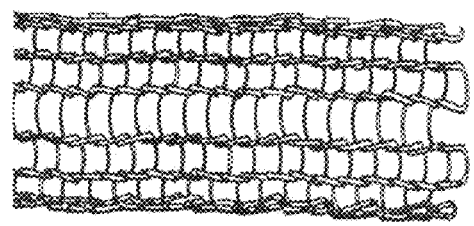

After production, the resulting wire 30 may then be braided into the shape of a stent such as that of FIG. 1A, knitted into the shape of a stent such as that of FIG. 1B, or otherwise formed into a medical device such as a vascular or gastric stent, aneurysm clotting device, or blood filter, for example. For the foregoing applications, wire 30 will typically be drawn to a final finish diameter between 20 μm and 250 μm.

The yield strength of wire 30, and thus its resilience, is controlled by the amount of strain-hardening deformation applied to wire 30 to achieve the final diameter and by the thermal treatment applied after drawing the wire. The ability to vary the strength and resilience of wire 30 allows use of the wire in resilient designs, such as for self-expanding stents, or for plastic-behaving designs, such as for balloon-expanding stents.

The selection of materials for shell 32 and core 34 will inherently determine the absolute and relative biodegradation rates of these materials, and may be chosen by one of ordinary skill in the art in accordance with such considerations. For example, the above-described materials for shell 32 may have a relatively slower biodegradation rate than the above-disclosed materials for core 34. It is also contemplated that antiferromagnetic alloys of iron and manganese may be used for magnetic resonance imaging compatibility.

Shell 32 of the wire may be partially or fully coated with a biodegradable polymer 35 (FIG. 2) that may be drug-eluting to further inhibit neointimal proliferation and/or restenosis. Suitable biodegradable polymers include poly-L lactic acid (PLLA) and poly-L glycolic acid (PLGA), for example. The wire may be coated either before, or after being formed into a stent.

In another embodiment, a monolithic biodegradable wire may be formed of iron or an iron alloy, such as an iron-manganese alloy, by the cold work processing described herein. As described in Example 1 below, this wire is formed to have a yield strength, such as at least 1375 MPa, for use in a stent.

Exemplary monolithic biodegradable wires, discussed in detail in the Examples section below, include the following materials: iron with 50% strain hardening (which may also be referred to in the present disclosure as Fe 50, Fe-50 or Fe-50CW); iron with 90% strain hardening (which may also be referred to in the present disclosure as Fe 90, Fe-90 or Fe-90CW); and iron with 99% strain hardening (which may also be referred to in the present disclosure as Fe 99, Fe-99 or Fe-99CW).

Wire Properties

As discussed in the Examples below, experimental results using wires made in accordance with the present disclosure were statistically compared to clinically-accepted design standards including 316L stainless steel, CoNiCr (also referred to as MP35N®, which is a registered trademark of SPS Technologies, Inc. of Jenkintown, Pa.), and Nitinol stent designs. The Experiments discussed in the Examples use nutrient metal wire designs comprising elements with known systemic tolerability and clearance pathways. In exemplary embodiments, the wire designs comprise varying proportions of iron (Fe) and magnesium (Mg), and cover an anticipated wide range of degradation rates associated with the unique electrochemical nature of the elements. It is also contemplated that manganese (Mn) and zinc (Zn) may be used, which in turn have their own inherent degradation rates.

The monolithic and bimetal composite biodegradable wires may have a ratio of yield strength to Young modulus of elasticity equal to at least 0.5%, or in other embodiments, at least 0.75%. This ratio is referred to in Table 4 (shown below in Example 1) as the "Resilience" of a material. In exemplary embodiments, the Resilience is as little as 0.46%, 0.54% or 0.62%, and as much as 0.95, 0.97 or 1.25%, or may be any value within any ratio defined by any of the foregoing values.

The monolithic and bimetal composite biodegradable wires may have a fatigue endurance of up to $10^7$ cycles at strain amplitudes of about 0.20, 0.23, 0.25, 0.28 or 0.30, or any value within any range defined by the foregoing values.

The bimetal composite wires may have sufficient ductility the render the wires able to be formed, without breaking, over a mandrel having a diameter 20 times the outside diameter of the bimetal composite wire. This high level of ductility may result from processing the wire in accordance with the present disclosure.

Figures 4A, 4B, 4C, 4D:
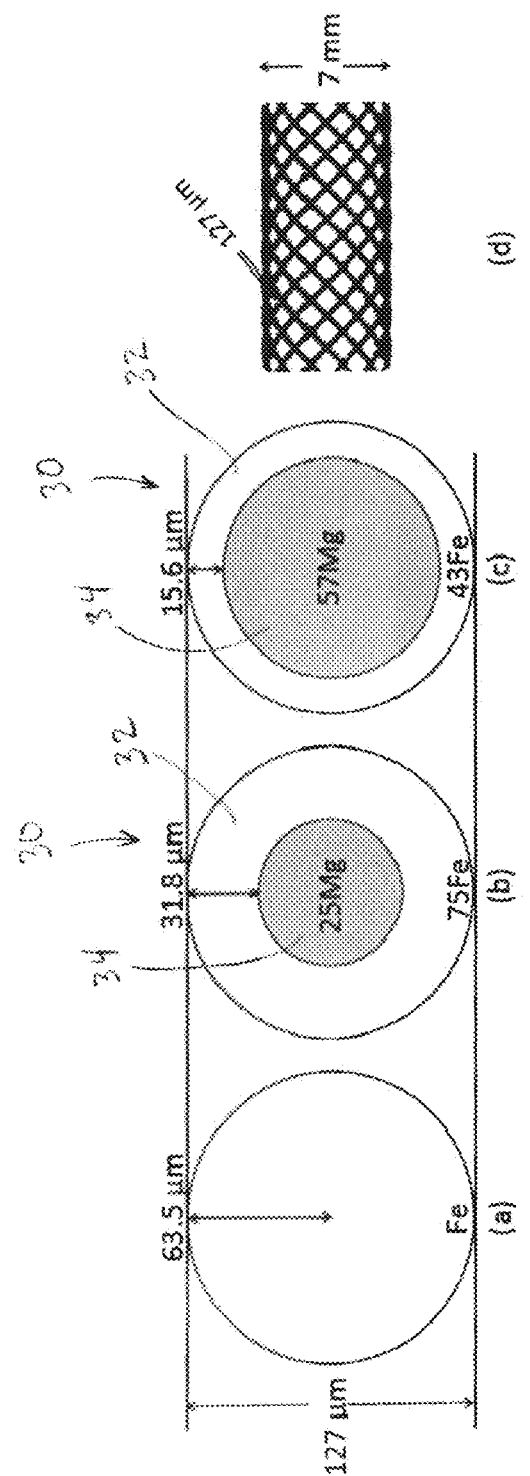
FIG. 4a is an elevation, cross-sectional view of a wire made from solid iron (Fe) of diameter 63.5 μm.
FIG. 4b is an elevation, cross-sectional view of a composite wire made from iron-magnesium (Fe-25 v/v % Mg) with a 31.8 μm-thick, relatively slowly degrading Fe or FeMn alloy-shell surrounding a relatively quickly degrading 63.5 μm-diameter Mg or Mg-2 wt % Zn-1 wt % Mn alloy core fiber.
FIG. 4c is an elevation, cross-sectional view of a composite wire made from iron-magnesium (Fe-57 v/v % Mg) comprising a 15.6 μm-thick Fe-shell surrounding a 95.8 μm-diameter Mg core fiber.
FIG. 4d is an elevation view illustrating the geometry of a braided 7 mm diameter stent comprising 24 wire elements formed into a mesh tubular scaffold, in accordance with the present disclosure.

As shown in FIGS. 4a-4c, the relative proportions of metals used in the experiments can be varied by varying the relative thicknesses of core 34 and shell 32. For example, FIG. 4a shows a monolithic iron-based stent, such as a pure-iron wire. FIG. 4b shows a stent with shell 32 comprising pure iron (Fe) and making up 75% of the total cross-sectional area of wire 30, and core 34 comprising pure magnesium (Mg) and making up the balance (25%) of the cross-sectional area of wire 30. FIG. 4c shows a stent with shell 32 comprising pure iron (Fe) and making up 43% of the total cross-sectional area of wire 30, and core 34 comprising pure magnesium (Mg) and making up the balance (57%) of the cross-sectional area of wire 30.

These materials, as well as the benchmark alloys including 316L stainless steel, MP35N® and NiTi were procured as 125 μm wire and 7 mm outside diameter, tubular mesh stent scaffolds manufactured from the said wire, from biomedical materials supplier, Fort Wayne Metals (Fort Wayne, Ind., USA). The effective strut thickness (wire diameter) of 127 μm and expanded tubular diameter of 7 mm, as per FIG. 3(d), are selected as dimensions similar to current self-expanding stent designs which are used in peripheral vessel scaffolding. It is also contemplated that magnesium WE43 alloy may be used.

Wire Biodegradation

In addition to material selection, the mechanical characteristics of wire 30 may be selected to determine its biodegradation rate. For example, the thicknesses of shell 32 and core 34 may be selected to control their biodegradation rates, with relatively thicker constructs requiring more time for biodegradation, and relatively thinner constructs requiring less time for biodegradation. Further, the geometry of the shell, core, and/or the overall formed device may result in certain regions of wire 30 being exposed to body tissue to a greater extent than other regions of wire 30, which may affect the biodegradation rates.

Mechanical-design-specific stent reaction forces act upon the tunica intima of blood vessels. This contact directly elicits a cellular response from the endothelium, thereby influencing the cell-blood interaction. Endothelial cells regulate important biological responses such as vasodilation, gene expression, and inflammatory signaling sequences in response to mechanotransduction pathways associated with stimulation by wall-shearing blood flow. The endothelium also shields blood from pro-inflammatory cytokines and pro-aggregatory adhesion molecules found in the sub-intimal layers. These processes depend upon complex signaling and feedback mechanisms which may be influenced by atherosclerotic disease, medical intervention, age and exercise. In view of these complex interactions between a stent and the surrounding biological and anatomic environment, stents and wires made in accordance with the present disclosure offer the ability to optimize design to account for anatomy, blood and cell compatibility, long term endothelial functionality, fracture resistance, and anatomy and patient-specific rates of bioabsorption.

Advantageously, wires and stents made in accordance with the present disclosure allow a surgeon to implant a naturally reactive stent over the long-term, thereby reducing late complications such as late-stent-thrombosis, relative vessel occlusion and lifelong anti-platelet therapy. When used in self-expanding, biocompatible, and biodegrading stent designs the present wire can further extend this ideal treatment option to the more-challenging vasculature of the extremities.

More specifically, bioabsorbable wires and stents made in accordance with the present disclosure can initially withstand flexion of mobile vessels of the extremities, give sufficient time for vessel remodeling, and then biodegrade. Thus, the present wire is ideally suited for use in stents implanted in high-flexion areas (i.e., extremities) and other demanding applications.

It is contemplated that stent designs incorporating wire of the present disclosure should install with low balloon pressures and exert chronically lower expansion forces. Ideal designs should also bio-absorb after vessel remodeling to promote uninhibited endothelial function and vasoreactivity as well as allowing future reintervention.

Yet another advantage of wire made in accordance with the present disclosure is the production of stents which are specifically designed for long term therapy in young patients. Such designs may focus on the accommodation of somatic growth and the enablement of future reintervention. The ideal stent for CHD may be one that bio-absorbs at a desired rate in order to avoid vessel recoil before adequate remodeling has occurred.

Still another advantage of the present wire is the opportunity to offer controllable degradation rates of stents to allow patient-dependent time for vessel remodeling. As noted above, patient-specific stent degradation rates also offer long-term benefit by allowing unimpeded reintervention and natural long term vasoreactivity.

Mechanical properties of wires made in accordance with the present disclosure can be controlled by various methods. For example, the composite tensile strength and toughness of Fe—Mg wire can be expected increase as a function of the fractional Fe-constituency. In addition, the mechanical fatigue durability of Mg wire can be expected to improve by compositing with Fe through enhanced surface resistance to plastic deformation in the cold work (CW) strain-hardened Fe exterior. Still further, magnesium constituency in Fe—Mg composite wires can be increased, with an expectation of a negligible decrease in observed flexural stiffness due to the relatively stiff Fe-cladding providing outer fiber support.

The degradation properties of wire made in accordance with the present disclosure may also be characterized and/or controlled. For example, the ratio of the maximum load at a given displacement and degradation time point to the non-degraded maximum load at equivalent displacement will give a quantitative indication of the residual mechanical integrity of the sample. In another example, a wire exposed to serum proteins is expected to experience a decrease in the rate of iron dissolution due to tight Fe surface-binding interactions and diminution of the clearance rate of degradation products.

The rate of degradation of bioabsorbable materials can be measured in a laboratory using a simulated bodily environment, e.g. saline or buffered-saline supplemented with various mammalian serums or serum proteins. Although this simplified measurement of the degradation rate may not accurately describe the true rate of degradation that would be observed in an implant subjected to in vivo conditions, such experimentation is useful to compare the degradation of different materials and material conditions.

Variables which are expected to impact the degradation rate of materials include pH or relative acidity, protein adsorption and/or binding, the immune response, fluid flow rate, local temperature, the local clearance rate of degradation byproducts and other complex variables such as stress-assisted corrosion, cellular adhesion, protein expression and fibrous encapsulation. When a solid foreign body is implanted, one of the first reactions to take place is protein adsorption; therefore, protein adsorption is expected to be an important variable in the initial degradation response. The quantity of protein adsorbed and the strength of the bond between the adsorbed proteins and the material are dependent upon the nature of the proteins and the chemical nature of the implant surface. In flowing human blood, two proteins that commonly adsorb to metallic and polymer surfaces include serum albumin and fibronectin. These proteins have been shown to adhere strongly to ferrous surfaces and this strong binding will likely create a protective barrier which reduces the evacuation of the iron-hydroxide and iron oxide based degradation products, thereby retarding the degradation rate of the metal. In support of this hypothesis, several past studies have disclosed rapid degradation rates of iron in plain saline environments, where thin metallic sections are consumed in a matter of hours or days under ex vivo laboratory study. In other studies, similarly dimensioned sections of iron or iron alloys have been shown to maintain structural integrity after greater than two years implantation in porcine and lapine vasculature.

The present wire constructs address this observation by reducing the iron or iron-alloy mass and strut thickness within a given stent construction by the introduction of a second more rapidly degrading material, as discussed above. The degradation of the present bioabsorbable wire construct will likely occur, at first, by degradation of the relatively slowly degrading species. If the outer shell is designed as the slowly degrading component, degradation will occur until some exposure of the relatively fast-degrading core. At this stage, e.g. in the case of a wire construct having an iron or iron alloy outer shell and a magnesium or magnesium core, an electrochemical potential will drive the more rapid degradation of the core. This intermediate degradation point will leave behind a thin iron or iron alloy outer shell which will possess reduced flexibility more similar to the vascular wall, thereby permitting more natural vessel movement and reactivity. Further, this thin outer shell of iron or iron-alloy will degrade more quickly than a comparable iron or iron alloy monolith.

In wire constructs having an outer shell formed of a more rapidly degrading material and a core formed of a more slowly degrading material, the degradation process is expected to consume the outer shell and leave an intermediate and mostly continuous core. Similar to the embodiment described above, this relatively thin core element will provide improved flexibility, an increased rate of bioabsorption, and a concomitantly improved vessel healing response with a reduced risk of thrombosis, particle embolization, and restenosis compared to a bioabsorbable monolith.

Biocompatibility of wires made in accordance with the present disclosure is also a characterizable and/or controllable wire property. For example, the well-known binding affinity of Fe to various proteins can be expected to foster an increased rate of cell attachment to iron-clad Fe—Mg composite wires compared to benchmark alloy systems. In another example, increasing concentration of dissolved Fe(II), Fe(III) and Mg(II) ions can be expected to result in an increased cytotoxic response compared to corrosion-resistant benchmark alloys. In yet another example, protein binding to the ferrous surface of Fe—Mg stents can be expected to promote cell adherence an enhanced vascular endothelialization by proliferation.

EXAMPLES

The following non-limiting Example illustrates various features and characteristics of the present invention, which is not to be construed as limited thereto.

Example 1

In this Example, exemplary bimetal composite wires and high strength iron monolith wires were produced, tested and characterized. In addition, three benchmark alloy wires were produced, tested and characterized for comparison to the exemplary wires.

1. Production of Bimetal Composite and Monolithic Wires

For Wire #1-3 in Tables 1 and 4 below, a pure Fe rod of dimension F mm outside diameter (OD) was processed as monolithic (solid) wire.

Similarly, for Wire #7-9 in Tables 3 and 4 below, 316L stainless steel, MP35N and Nitinol alloy wire respectively, of dimension H mm outside diameter (OD) were processed as monolithic wire.

For Wire #4-6 in Tables 2 and 4 below, a pure Fe tube of dimension A mm outside diameter (OD) x dimension B mm inside diameter (ID) was filled and drawn down over dimension C mm outside diameter (OD) pure Mg rod to create a first composite having the area fraction specified. Value D is the area fraction as defined by the ratio of the core area to overall wire area.

All wires were repetitively drawn and annealed, with appropriate levels of strain hardening to impart relatively high strength to the resulting wire product, to a final nominal finish OD of 125 μm, and the wires were spooled. The tensile strength properties of the wires were measured in a uniaxial tensile test on an Instron Model 5565 test machine at 24° C. in ambient shop air.

TABLE 1

| | Exemplary monolithic wires | | |
|---|---|---|---|
| Wire # | Starting Size, mm (F) | Finish Diameter, mm (G) | Material Designation |
| 1 | 12.7 | 0.127 | Fe-50 |
| 2 | 12.7 | 0.127 | Fe-90 |
| 3 | 12.7 | 0.127 | Fe-99 |

TABLE 2

Exemplary DFT wires

| Wire # | Tube OD, mm (A) | Tube ID, mm (B) | Core ID, mm (C) | Core Ratio, % (D) | Finish Diameter, mm (E) | Material Designation |
|---|---|---|---|---|---|---|
| 4 | 10 | 7 | 3.2 | 25 | 0.127 | Fe-DFT-25% Mg |
| 5 | 5 | 4 | 3.2 | 25 | 0.127 | Fe-DFT-57% Mg |
| 6 | 11.5 | 5.8 | 5.4 | 25 | 0.127 | Fe35Mn-DFT-25% MgZM21 |

TABLE 3

Monolithic benchmark alloy wires

| Wire # | Starting Size, mm (H) | Finish Diameter, mm (I) | Material Designation |
|---|---|---|---|
| 7 | 2.5 | 0.127 | 316L |
| 8 | 1.6 | 0.127 | MP35N |
| 9 | 2.1 | 0.127 | Nitinol |

The tensile strength properties observed are similar to those of known materials such as Co—Ni—Cr/Tantalum composite wires used in stent designs and therefore are expected to be suitable for subsequent forming and wall support functionality.

Figure 5:
FIG. 5 is a picture of a braided stent structure formed from wire made in Example 1.
Figure 6A:
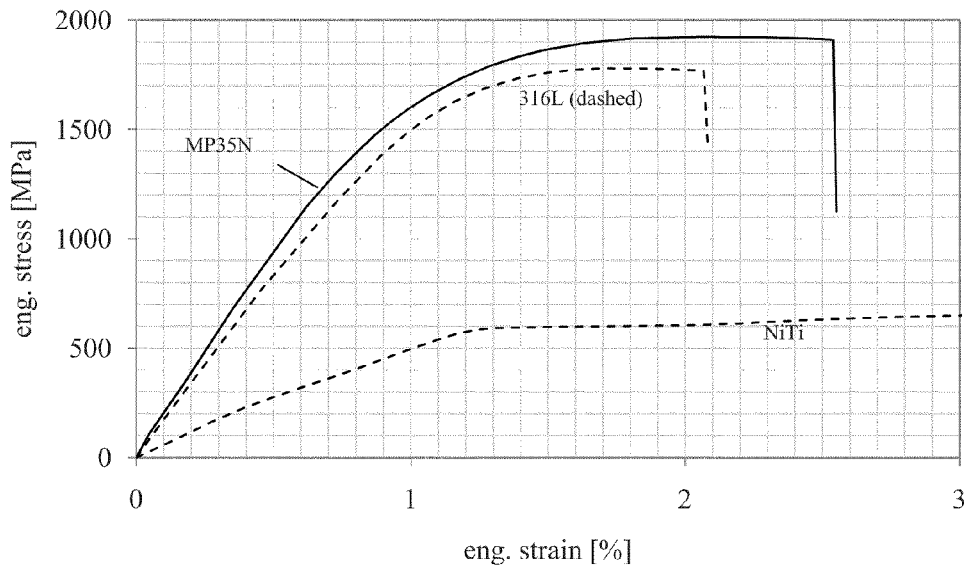
FIG. 6a is a graph illustrating tensile test results for sample materials used in Example 1, including engineering stress-strain plots for benchmark wire samples.
Figure 6B:
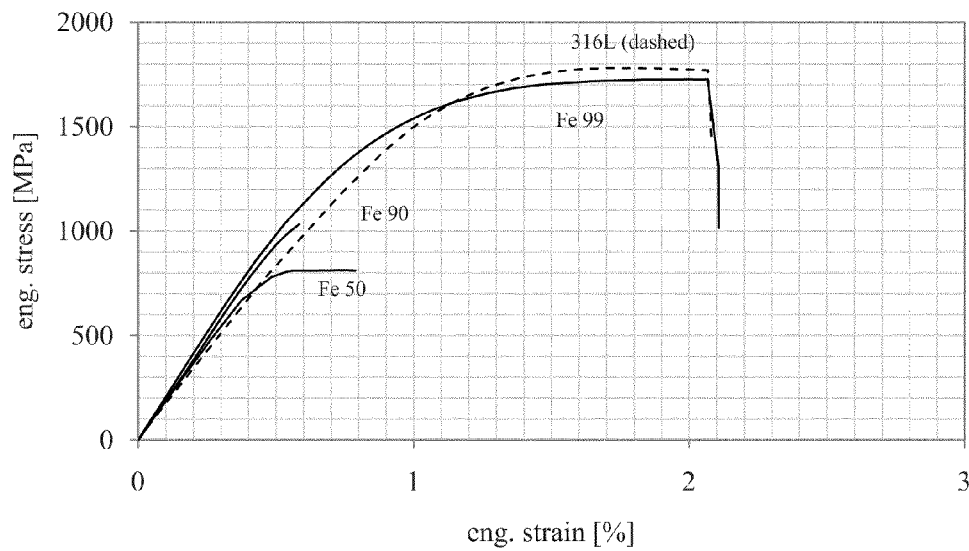
FIG. 6b is a graph illustrating tensile test results for sample materials used in Example 1, including engineering stress-strain plots for exemplary monolith wire samples.
Figure 6C:
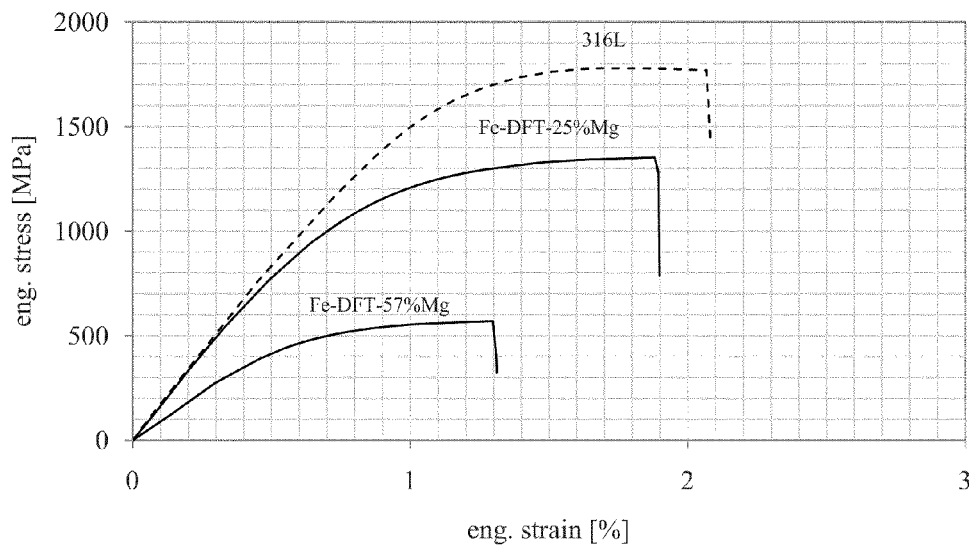
FIG. 6c is a graph illustrating tensile test results for sample materials used in Example 1, including engineering stress-strain plots for exemplary bimetal wire samples.
Figure 6D:
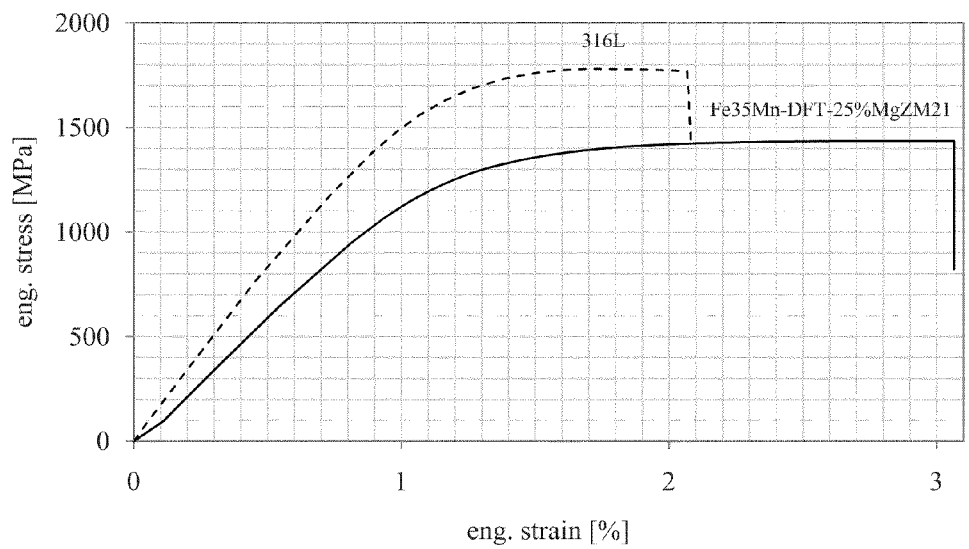
FIG. 6d is a graph illustrating tensile test results for sample materials used in Example 1, including engineering stress-strain plots for additional exemplary bimetal wire samples.

Several hundred meter lengths of the wires were also successfully braided into a 24 wire count, 90° braid angle, Ø5 mm ID tubular stent structures shown in FIG. 5, suitable for use as an arterial support structure similar to the stent shown in FIG. 1A.

2. Characterization of Mechanical Properties in Tension, Flexure and Cyclic Loading In this Example, mechanical testing is performed on exemplary bimetal composite and monolithic wires, and mechanical properties of the wires are characterized.

In order to maximize therapeutic benefit, any vessel scaffold should be able to mechanically withstand both the static and pulsatile dynamic radial forces exerted by the wall after implantation. The static strength of the scaffold will ideally be sufficient to prevent acute recoil and negative remodeling for at least 3-6 months after implantation. Pulsatile loading associated with the beating heart will impart $10^7$ load cycles during this period of remodeling. In order to ensure suitable material strength, material systems are tested and compared against materials which are used routinely in clinical practice such as 316L stainless steel, cobalt-chrome-moly alloy (CoNiCr, or MP35N®) and Nitinol shape memory alloy (NiTi). The aim of testing is to benchmark these alloys via uniaxial tension and durability against cyclic flexural fatigue damage.

a. Tensile Strength

The composite tensile strength and toughness of exemplary wires in accordance with the present disclosure is expected to increase as a function of the fractional Fe-constituency.

i. Experimental Technique: Tensile Testing

Destructive uniaxial tension testing of the wire materials is used to quantify the ultimate strength, yield strength, axial stiffness and ductility of candidate materials, using methods described in Structure-Property Relationships in Conventional and Nanocrystalline NiTi Intermetallic Alloy Wire, *Journal of Materials Engineering and Performance* 18, 582-587 (2009) by Jeremy E. Schaffer, the entire disclosure of which is hereby expressly incorporated herein by reference. These tests are run using servo-controlled Instron load frames in accordance with industry standards for the tension testing of metallic materials.

Bioabsorbable and benchmark alloy wires are destructively tested in a monotonic, single tensile load-increasing cycle, at 25° C. at a strain rate of $10^{-3}$ $s^{-1}$ using an Instron Model 5500 series load frame (Instron, Norwood, Mass., USA).

ii. Results

FIGS. 6a-6d are plots of stress-strain data for individual 125 μm wire.

Figure 7A:
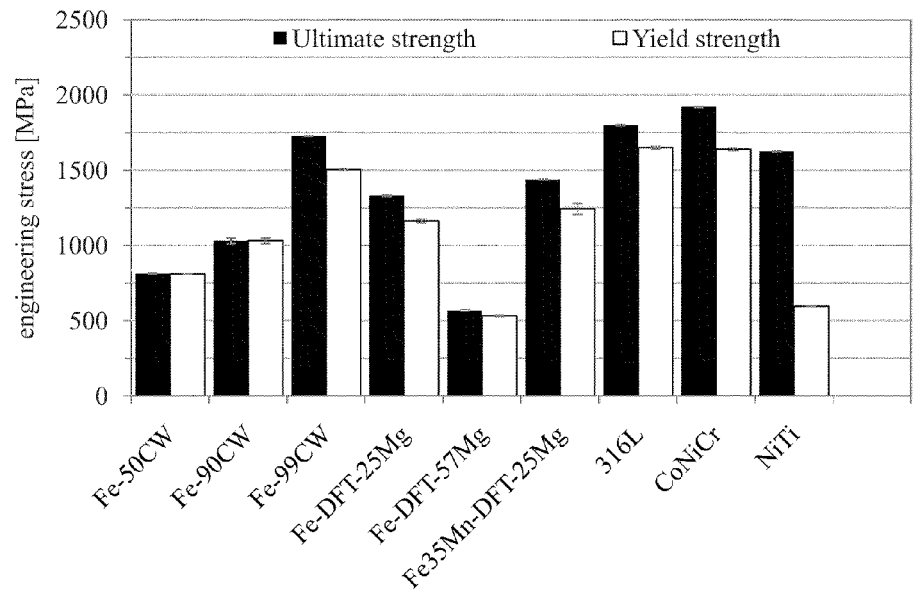
FIG. 7a is a graph illustrating computed ultimate tensile strength, in which error bars indicate one standard deviation.
Figure 7B:
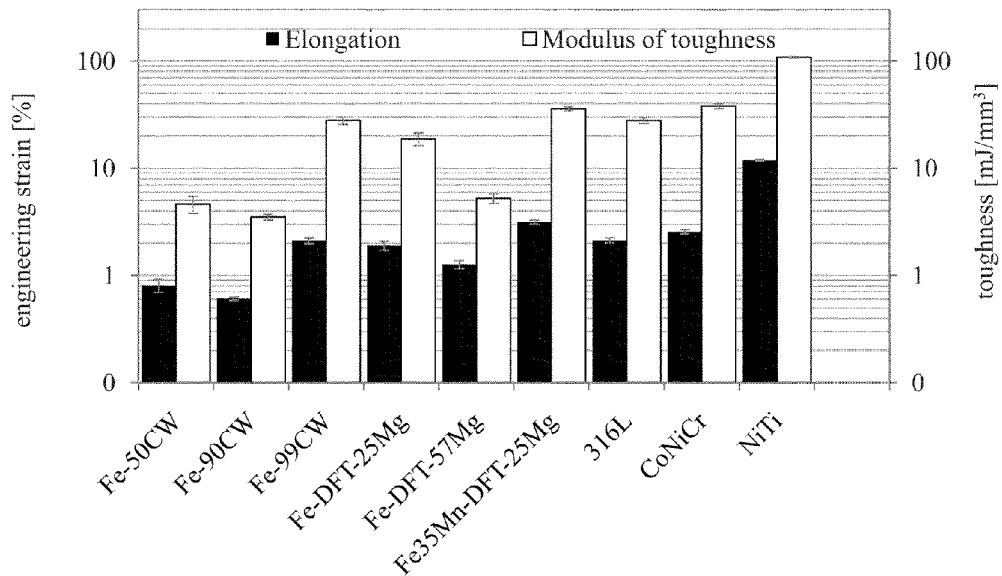
FIG. 7b is a graph illustrating computed elongation and modulus of toughness, in which error bars indicate one standard deviation.
Figure 7C:
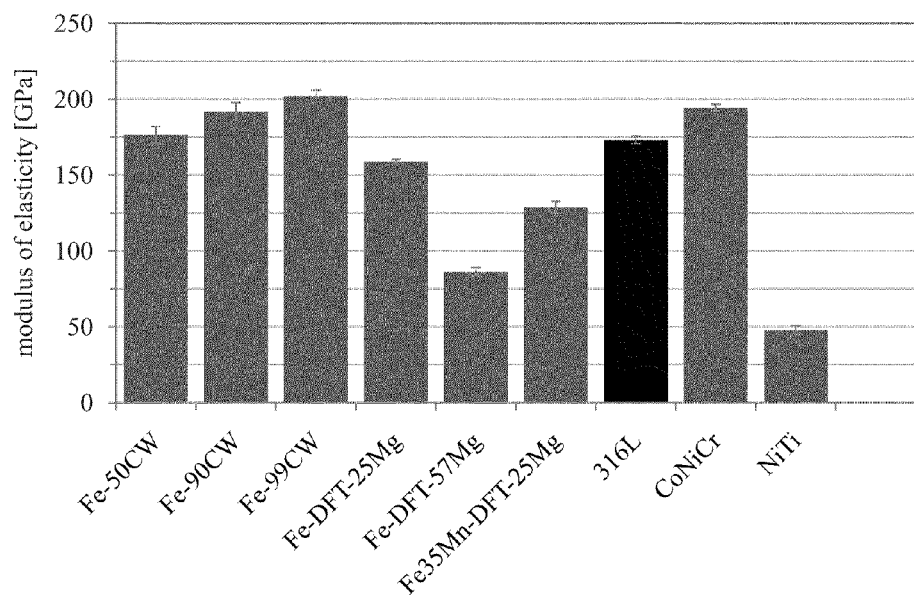
FIG. 7c is a graph illustrating computed Young's modulus of elasticity, in which error bars indicate one standard deviation.

Ultimate tensile strength, yield strength, elongation at rupture, modulus of elasticity and modulus of toughness were calculated from similar plots for each sample tested at six breaks per sample (N=6). The results of such testing are summarized in FIGS. 7a-7c, in which illustrated error bars are equivalent to one standard deviation, and presented in Table 4 below. Table 4 includes numerical values for the data presented graphically in FIGS. 7a-7c, and standard deviation in parentheses below each value.

TABLE 4

Mechanical Property Data For Nominally 125 μm (Ø.005") Bimetal Composite, Iron Monolith and Benchmark Wires.

| Wire #- Material | Ultimate strength $S_U$ [MPa] | Yield strength $S_Y$ [MPa] | Elongation $e_R$ [%] | Young's Modulus of Elasticity E [GPa] | Modulus of Toughness $E_T$ [mJ/mm³] | Resilience $S_Y/E$ [%] |
|---|---|---|---|---|---|---|
| 1 - Fe-50 | 813 (2.36) | 810 (2.21) | 0.809 (0.110) | 177 (5.4) | 4.64 (0.82) | 0.46 (0.0013) |
| 2 - Fe-90 | 1032 (18.9) | 1032 (18.9) | 0.609 (0.022) | 192 (6.0) | 3.52 (0.21) | 0.54 (0.0102) |
| 3 - Fe-99 | 1728 (0.79) | 1505 (5.73) | 2.12 (0.130) | 202 (4.0) | 27.9 (2.3) | 0.75 (0.0029) |

TABLE 4-continued

Mechanical Property Data For Nominally 125 μm (Ø.005") Bimetal Composite, Iron Monolith and Benchmark Wires.

| Wire #- Material | Ultimate strength $S_U$ [MPa] | Yield strength $S_Y$ [MPa] | Elongation $e_R$ [%] | Young's Modulus of Elasticity E [GPa] | Modulus of Toughness $E_T$ [mJ/mm$^3$] | Resilience $S_Y/E$ [%] |
|---|---|---|---|---|---|---|
| 4 - Fe-DFT-25% Mg | 1332 (4.25) | 1163 (10.1) | 1.90 (0.189) | 159 (1.7) | 18.8 (2.5) | 0.73 (0.0065) |
| 5 - Fe-DFT-57% Mg | 570 (2.47) | 532 (4.34) | 1.27 (0.107) | 86 (2.9) | 5.23 (0.54) | 0.62 (0.0052) |
| 6 - Fe35Mn-25% MgZM21 | 1439 (2.66) | 1243 (36.2) | 3.16 (0.142) | 129 (4.0) | 35.8 (1.6) | 0.97 (0.0290) |
| 7 - 316L | 1801 (1.76) | 1650 (7.81) | 2.13 (0.100) | 173 (2.4) | 27.9 (1.8) | 0.95 (0.0046) |
| 8 - MP35N ® | 1922 (2.45) | 1640 (9.89) | 2.56 (0.109) | 194 (2.1) | 38.1 (2.0) | 0.84 (0.0051) |
| 9 - Nitinol | 1626 (1.34) | 596 (3.48) | 11.9 (0.088) | 48 (2.8) | 108 (1.6) | 1.25 (0.0077) |

As set forth in Table 4, tensile test data show that the mechanical properties of the exemplary monolithic wires are comparable and/or statistically similar to the benchmark non-biodegradable materials including 316L stainless steel wire.

The ultimate tensile strength and stiffness of the exemplary bimetal composite wires were intermediate, falling below 316L. The modulus of toughness of the Fe-DFT-25% Mg and Fe35Mn-25% MgZM21 composites, at 18.8 mJ/mm$^3$ and 35.8 mJ/mm$^3$ respectively, were similar to that of benchmark 316L and MP35N (27.9 mJ/mm$^3$ and 38.1 mJ/mm$^3$, respectively).

b. Fatigue Resistance

The mechanical fatigue durability of in vivo wires made in accordance with the present disclosure can be expected to improve by compositing with Fe or Fe alloy through enhanced surface resistance to plastic deformation in the cold work (CW) strain-hardened Fe exterior.

i. Experimental Technique: Rotary Beam Fatigue Testing

Candidate material durability was empirically determined by testing to failure under cyclic load conditions using rotary beam fatigue testing methods as described in *Structure-Property Relationships in Conventional and Nanocrystalline NiTi Intermetallic Alloy Wire*, incorporated by reference above. These tests are run using A/C synchronous motor-driven, rotary, load frames achieving a cyclic rate of 60 Hz. The tests are initially run in ambient lab air at 24±3° C. at a load ratio, defined as the ratio of the minimum to maximum load strain, of R=−1 to rupture or cessation of testing at 10$^7$ cycles. From these data, namely the number of cycles to failure and load strains, Woehler load-life diagrams are computed and compared against the benchmark alloy systems.

125 μm bioabsorbable and benchmark alloy samples are loaded into a motor driven pin vise and elastically loaded to a geometrically defined strain level according to:

$\epsilon_{amp}=d/(d+D)$, where the strain amplitude ($\epsilon_{amp}$) is defined by the wire diameter, d, and the bend diameter, D. Samples are rotated at 3600 rpm in ambient air (T=23±3° C.) until rupture is achieved or until test termination at 10$^7$ cycles.

ii. Results

Figure 8A:
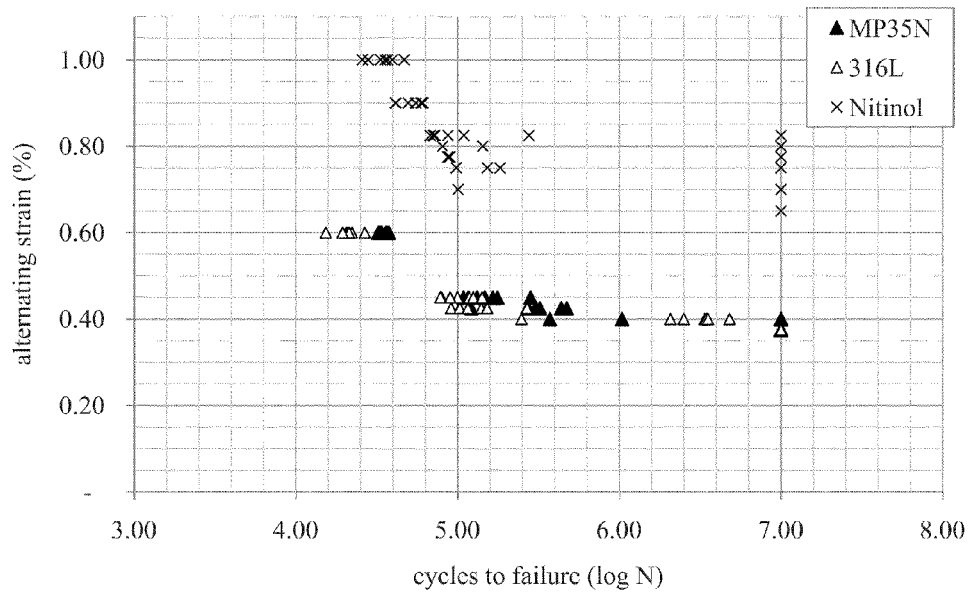
FIG. 8a is a strain-life diagram for three monolithic materials which serve as benchmarks, with alternating strain defined as the difference between the maximum and mean strain (R=−1) plotted against the log of failure lifetimes (N) for samples tested at 60 Hz in ambient air having temperature=23±3° C.
Figure 8B:
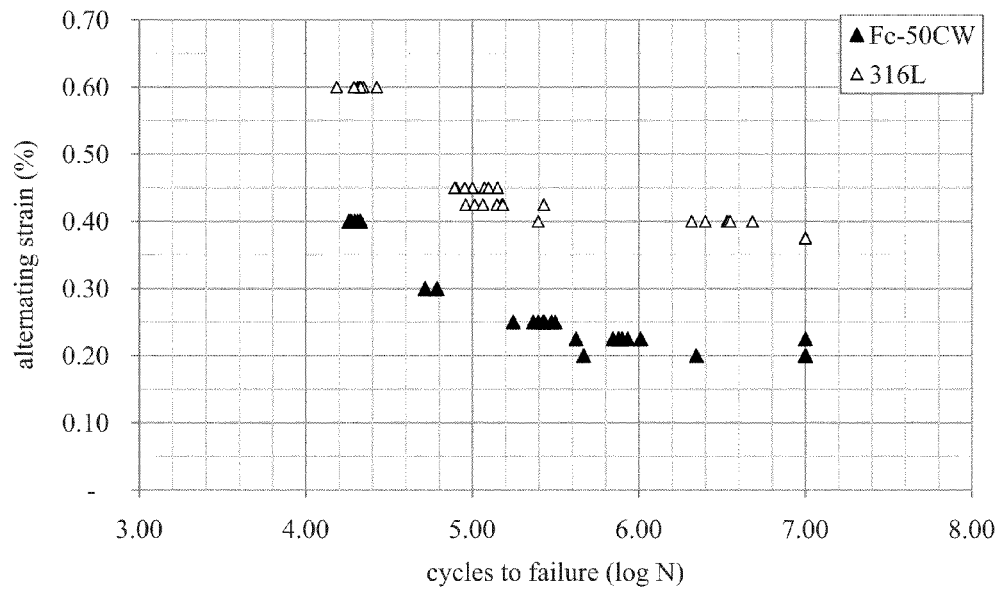
FIG. 8b is a strain-life diagram similar to the diagram of FIG. 8a, illustrating test results for monolithic Fe with a 50% strain-hardening preparation, as compared with the 361L stainless steel benchmark.
Figure 8C:
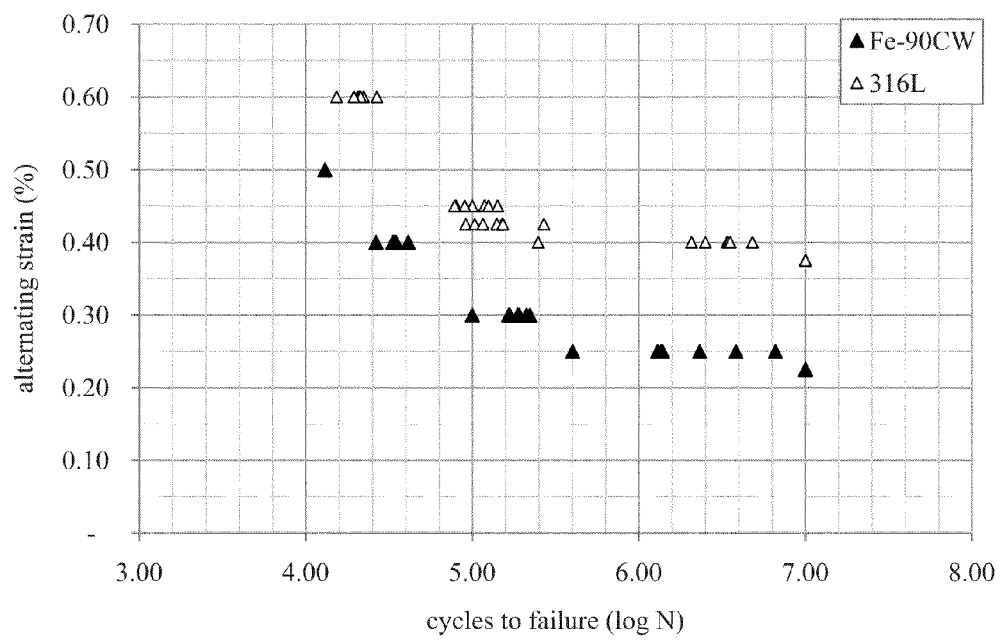
FIG. 8c is a strain-life diagram similar to the diagram of FIG. 8a, illustrating test results for monolithic Fe with a 90% strain-hardening preparation, as compared with the 361L stainless steel benchmark.
Figure 8D:
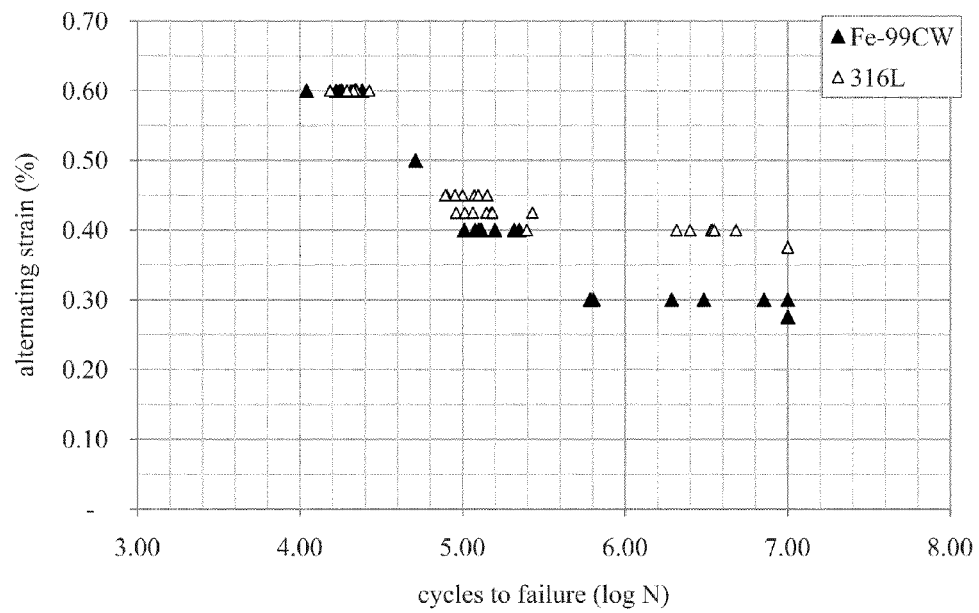
FIG. 8d is a strain-life diagram similar to the diagram of FIG. 8a, illustrating test results for monolithic Fe with a 99% strain-hardening preparation, as compared with the 361L stainless steel benchmark.
Figure 8E:
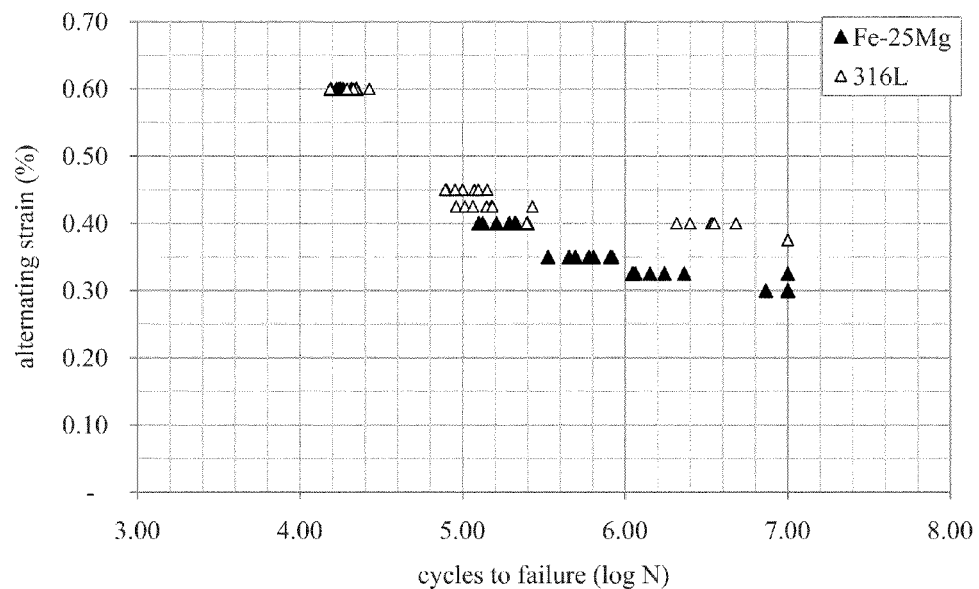
FIG. 8e is a strain-life diagram similar to the diagram of FIG. 8a, illustrating test results for bimetal composite Fe-25Mg material, as compared with the 361L stainless steel benchmark.
Figure 8F:
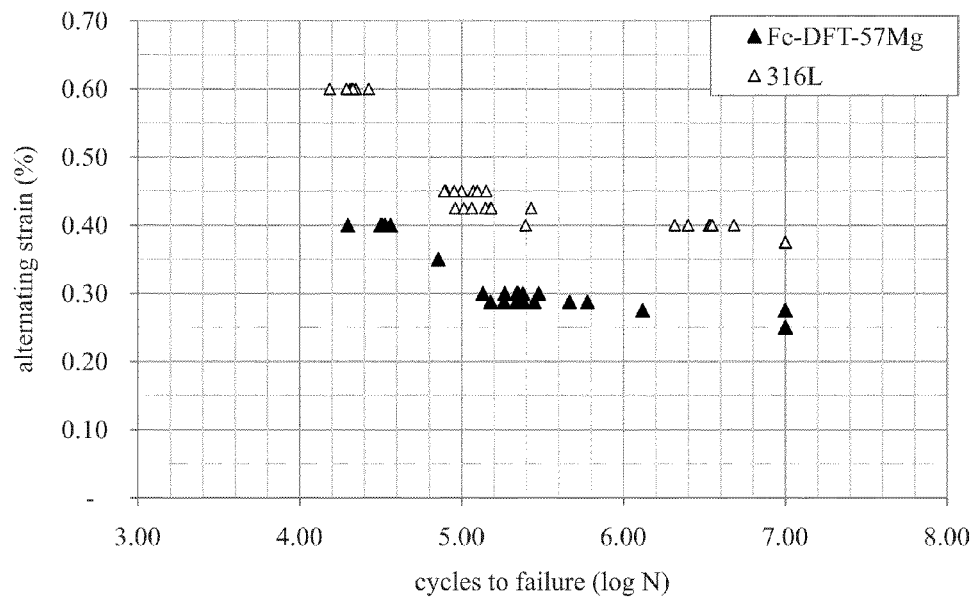
FIG. 8f is a strain-life diagram similar to the diagram of FIG. 8a, illustrating test results for bimetal composite Fe-DFT-57Mg material, as compared with the 361L stainless steel benchmark.
Figure 8G:
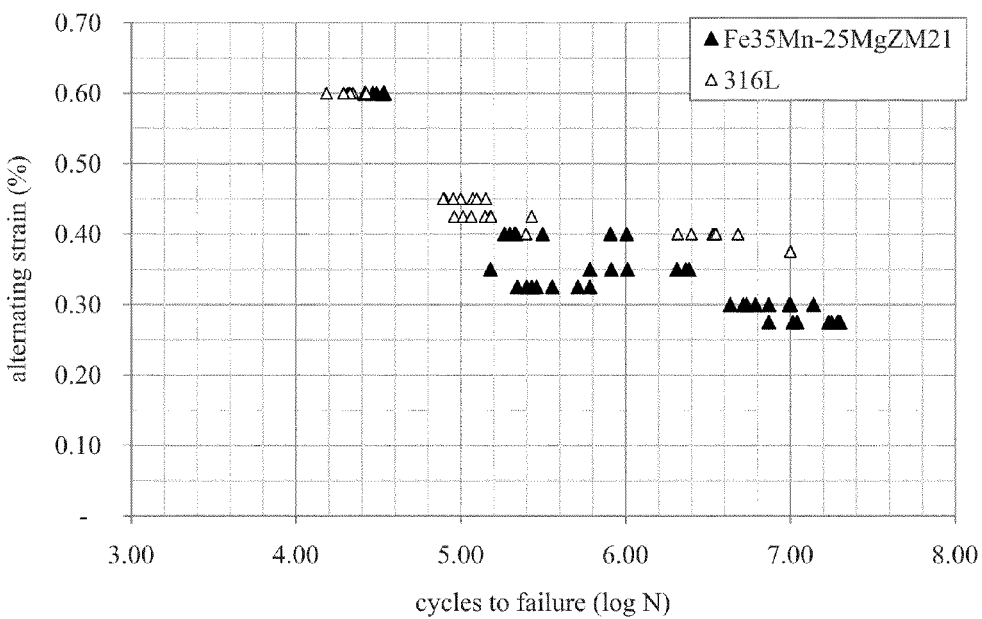
FIG. 8g is a strain-life diagram similar to the diagram of FIG. 8a, illustrating test results for bimetal composite Fe35Mn-25MgZM21 material, as compared with the 361L stainless steel benchmark.

FIGS. 8a-8g show a summary of the results plotted in a strain amplitude-life diagram. FIG. 8a shows results for three benchmark monolithic wires. FIGS. 8b-8d show results for exemplary monolithic wires prepared in accordance with the present disclosure, as compared to the benchmark 316L stainless material. FIGS. 8e-8g show results for exemplary bimetal composite wires prepared in accordance with the present disclosure, as compared to the benchmark 316L stainless material.

At 10$^7$ cycles (i.e., "log 7.00" cycles in the nomenclature of FIGS. 8a-8g), the fatigue strength the exemplary monolithic and bimetal composite materials (i.e., from about 0.2% strain to above 0.3% strain) was comparable to 316L (0.37% strain).

Commercially available 316L BX stents utilize relatively soft-annealed metal, with alternating strain limits at 10$^7$ cycles of approximately 0.2%, similar to the lowest fatigue strength found for the exemplary materials for iron with 50% strain hardening (or "CW" meaning "cold work").

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bimetal composite wire, comprising:
   a drawn outer shell formed of a first biodegradable metallic material, said shell defining an inner shell diameter and an outer shell diameter; and
   a drawn inner core formed of a second biodegradable metallic material, said inner core defining an outer core diameter,
   said first and second biodegradable metallic materials being different from one another whereby said first and second biodegradable metallic materials have differing biodegradation rates, and
   said inner shell diameter of said outer shell substantially equal to said outer core diameter such that, when viewed in section, said inner core completely fills said outer shell, said outer shell formed as a uniform and continuous jacket such that said wire may be coiled, braided, or stranded.

2. The bimetal composite wire of claim 1, wherein said first biodegradable material is selected from the group consisting of pure metallic iron (Fe) and an iron-based alloy (Fe alloy), and said second biodegradable material is selected from the group consisting of pure magnesium (Mg) and a magnesium-based alloy (Mg alloy).

3. The bimetal composite wire of claim 1, wherein said first biodegradable material is selected from the group consisting of pure magnesium (Mg) and a magnesium-based alloy (Mg alloy), and said second biodegradable material is selected from the group consisting of pure metallic iron (Fe) and an iron-based alloy (Fe alloy).

4. The bimetal composite wire of claim 1, having a ratio of yield strength to elastic modulus of at least 0.5%.

5. The bimetal composite wire of claim 1, having a fatigue strength of $10^7$ cycles at an alternating strain level of 0.2.

6. The bimetal composite wire of claim 1, having a ductility characterized by the ability to form the wire over a mandrel diameter equal to or less than 20 times the outside diameter of the bimetal composite wire.

7. The bimetal composite wire of claim 1, having:
a ratio of yield strength to elastic modulus of at least 0.5%;
a fatigue strength of $10^7$ cycles at an alternating strain level of 0.2; and
a ductility characterized by the ability to form the wire over a mandrel diameter equal to or less than 20 times the outside diameter of the bimetal composite wire.

8. A stent made of the bimetal composite wire of claim 1.

9. A bimetal composite wire, comprising:
a drawn outer shell comprising a first biodegradable metallic material, said outer shell making up a percentage of a total cross-sectional area within an outer shell diameter defined by said outer shell; and
a drawn inner core comprising a second biodegradable metallic material, said inner core making up the balance of the total cross-sectional area,
said first and second biodegradable metallic materials being different from one another whereby said first and second biodegradable metallic materials have differing biodegradation rates.

10. The bimetal composite wire of claim 9, wherein:
said outer shell defines an inner shell diameter, and
said inner core defines an outer core diameter,
said inner shell diameter of said outer shell substantially equal to said outer core diameter such that, when viewed in section, said inner core completely fills said outer shell.

11. The bimetal composite wire of claim 9, wherein said inner core comprises a solid metallic wire core and said outer shell comprises a tube.

12. The bimetal composite wire of claim 9, wherein said first biodegradable material is selected from the group consisting of pure metallic iron (Fe) and an iron-based alloy (Fe alloy), and said second biodegradable material is selected from the group consisting of pure magnesium (Mg) and a magnesium-based alloy (Mg alloy).

13. The bimetal composite wire of claim 9, wherein said first biodegradable material is selected from the group consisting of pure magnesium (Mg) and a magnesium-based alloy (Mg alloy), and said second biodegradable material is selected from the group consisting of pure metallic iron (Fe) and an iron-based alloy (Fe alloy).

14. The bimetal composite wire of claim 9, wherein said outer shell diameter is between 20 μm and 250 μm.

15. A bimetal composite wire, comprising:
a drawn outer shell formed of a first biodegradable metallic material, said outer shell comprising a tube defining an inner shell diameter and an outer shell diameter and making up a percentage of a total cross-sectional area of said wire; and
a drawn inner core formed of a second biodegradable metallic material, said inner core comprising a solid metallic wire defining a core diameter and making up the balance of the cross-sectional area of said wire,
said first and second biodegradable metallic materials being different from one another whereby said first and second biodegradable metallic materials have differing biodegradation rates,
said inner shell diameter of said outer shell substantially equal to said outer core diameter of said inner core such that, when viewed in section, said inner core completely fills said outer shell, and
said bimetal wire comprising a continuous wire structure capable of being spooled.

16. The bimetal composite wire of claim 15, wherein said first biodegradable material is selected from the group consisting of pure metallic iron (Fe) and an iron-based alloy (Fe alloy), and said second biodegradable material is selected from the group consisting of pure magnesium (Mg) and a magnesium-based alloy (Mg alloy).

17. The bimetal composite wire of claim 15, wherein said first biodegradable material is selected from the group consisting of pure magnesium (Mg) and a magnesium-based alloy (Mg alloy), and said second biodegradable material is selected from the group consisting of pure metallic iron (Fe) and an iron-based alloy (Fe alloy).

18. The bimetal composite wire of claim 1, wherein said outer shell makes up a percentage of a total cross-sectional area of said wire, and said inner core makes up the balance of the cross-sectional area of said wire.

19. The bimetal composite wire of claim 1, wherein said outer shell comprises a tube and said inner core comprises a solid metallic wire core.

20. The bimetal composite wire of claim 1, wherein said outer shell diameter is between 20 μm and 250 μm.

* * * * *